United States Patent [19]

Chimenti et al.

[11] Patent Number: 5,301,125
[45] Date of Patent: Apr. 5, 1994

[54] SPECTROSCOPIC DETERMINATION OF AMOUNT OF ONE CONSTITUENT OF A FLUID MIXTURE IN ANOTHER CONSTITUENT OR IN THE FLUID MIXTURE ITSELF, FOLLOWING SEPARATION OF THE MIXTURE INTO ITS CONSTITUENTS

[75] Inventors: Robert J. L. Chimenti, Short Hills; Gerald M. Halpern, Bridgewater, both of N.J.

[73] Assignee: Exxon Research & Engineering Company, Florham Park, N.J.

[21] Appl. No.: 588,649

[22] Filed: Sep. 26, 1990

[51] Int. Cl.$^5$ .............................................. G06F 15/20
[52] U.S. Cl. ...................................... 364/498; 208/28; 208/29; 208/30; 208/31; 208/32; 364/497; 364/502
[58] Field of Search ...................... 208/28, 29, 30, 31, 208/32; 364/497, 498, 502, 550

[56] References Cited

U.S. PATENT DOCUMENTS

| | | | |
|---|---|---|---|
| 2,994,646 | 8/1961 | Kleiss | 364/502 X |
| 3,079,079 | 2/1963 | Phister, Jr. et al. | 364/502 |
| 3,428,796 | 2/1969 | Martens et al. | 364/498 X |
| 4,449,819 | 7/1991 | Krause | 356/300 |
| 4,824,553 | 4/1989 | Rueff | 208/32 |
| 5,015,357 | 5/1991 | Rueff | 208/32 |
| 5,180,483 | 1/1993 | Braams et al. | 208/28 |

FOREIGN PATENT DOCUMENTS 3625490 2/1988 Fed. Rep. of Germany .
2020009 11/1979 United Kingdom .

*Primary Examiner*—Edward R. Cosimano
*Attorney, Agent, or Firm*—Jay Simon

[57] ABSTRACT

A method (and apparatus) is disclosed for the spectroscopic determination of the amount $a_{Nn}$ of one constituent N of a fluid mixture 0 in another constituent n of the mixture, following separation of the mixture into its constituents 1,..., M (where n, N≦M). The method involves determining the absorptivities an (n=1,...,N) of the M constituents from spectroscopic measurements and computing the amount $a_{Nn}$ from a mathematical expression containing the absorptivities $a_n$ and $a_N$ which are expressed or expressible as the quotient $a_n/a_N$ only. The method is insensitive to changes in the absorptivities due to feed variability or changes in upstream process conditions, since any changes in the numerator and denominator of the quotient used are affected correspondingly. A modification to the method involves determining the content $a_{N0}$ of constituent N in feed 0 from a mathematical expression containing $a_0$, where $a_0$ is the absorptivity of the feed 0, and $a_N$, which absorptivities $a_0$ and $a_N$ are expressed or expressible as the quotient $a_0/a_N$ only.

13 Claims, 6 Drawing Sheets

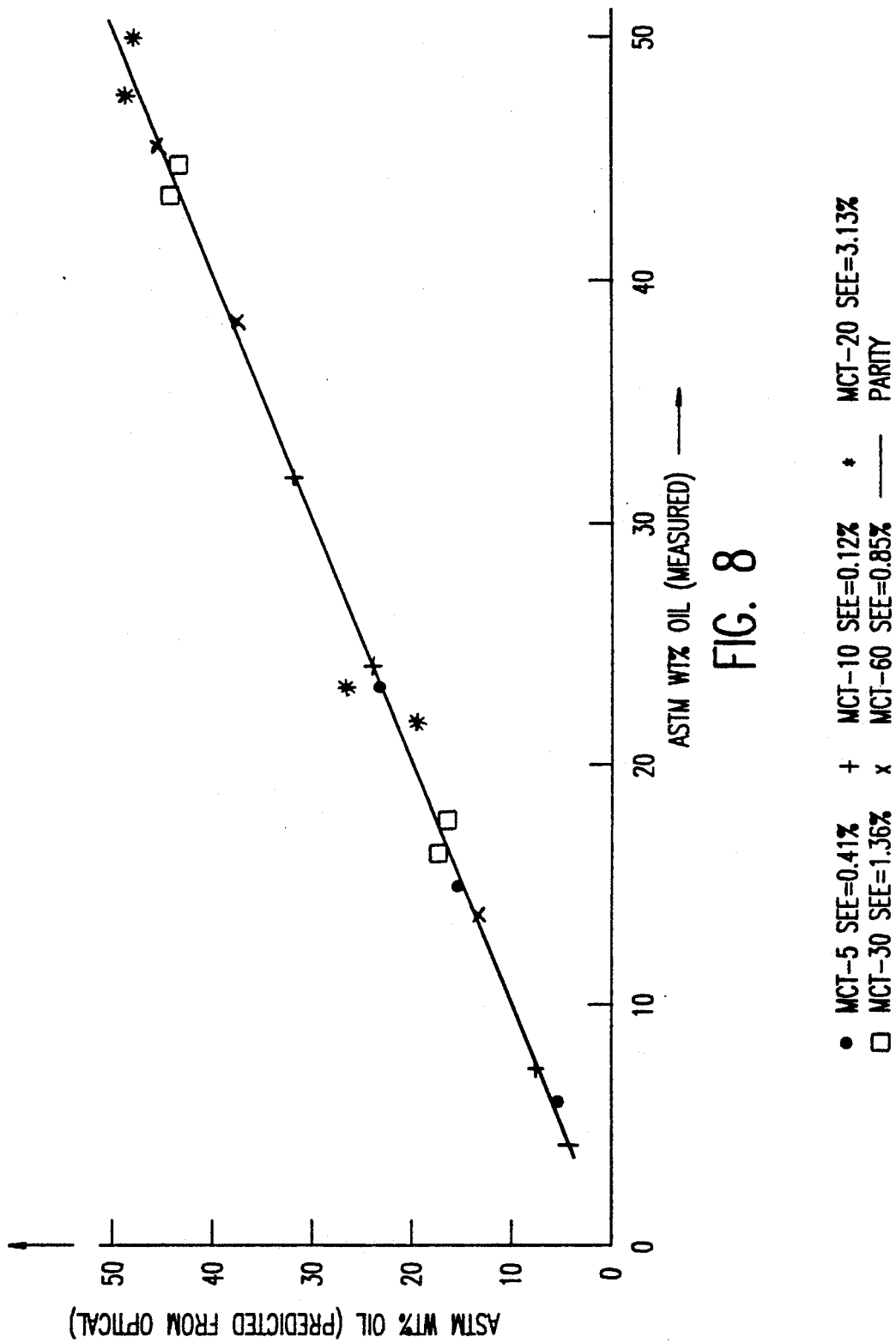

SPECTROSCOPIC DETERMINATION OF AMOUNT OF ONE CONSTITUENT OF A FLUID MIXTURE IN ANOTHER CONSTITUENT OR IN THE FLUID MIXTURE ITSELF, FOLLOWING SEPARATION OF THE MIXTURE INTO ITS CONSTITUENTS

BACKGROUND OF THE INVENTION

This invention relates to a method for the spectroscopic determination of the amount of one constituent of a fluid mixture (e.g., a liquid mixture) in another constituent of the mixture following the separation of the mixture into its constituents. More particularly though not exclusively, the invention relates to the determination of the entrained oil content of wax resulting from the separation, in a dewaxing filter, of a waxy raffinate into dewaxed hydrocarbon oil boiling in the lubricating oil range (hereinafter "dewaxed oil" or DWO) and wax. A modification of the invention relates to measuring the amount of one constituent in the fluid mixture. The amount of the one constituent in the other constituent or in the fluid mixture itself can be expressed as a molar, weight or volume percentage, fraction, or ratio, or an actual weight or volume if the corresponding weight or volume of the other constituent or feed were also known. A particular advantage of the invention is that the method is insensitive to changes in the feed composition or upstream process conditions, as will be explained in more detail hereinbelow.

Petroleum distillates obtained at atmospheric pressure and at temperatures above 370° C., and from further vacuum distillation, can be converted into lubricating oil basestocks. The conversion can be achieved through solvent extraction of a portion of the aromatic species present in the oil, followed by solvent dewaxing, or through other techniques, well-known in the art. Further processing, such as deoiling of the wax, may also be carried out.

In the dewaxing process, the wax is caused to precipitate from the waxy feed at a particular temperature, solvent, and solvent-to-oil ratio, and is separated from the oil by filtration. Oil may be entrained in the wax during this process. Economic credits may be obtained by optimizing the entrained oil content of the wax.

Several standard tests can be used to measure the entrained oil content. For example two tests of the American Society of Testing Materials, ASTM D721 and D3235, are currently used to determine the oil content of wax for sale. The ASTM D721 test serves as the American industry definition of the oil content of wax for oil levels below 15 wt %. Neither test, however, gives an accurate measure of the entrained oil content, since the tests report as oil the solvent-extractable portion of the wax at the test conditions. This material is not necessarily the same as the entrained oil in the wax, in quantity or composition, since the solvent and extraction conditions used in the ASTM tests may differ significantly from those used in the plant dewaxing.

In general, under the ASTM test conditions, not all of the wax is insoluble and not all of the oil is soluble. Consequently, for lower temperature distillation fractions, comprising lower molecular weight species, the ASTM tests are likely to report more oil than is actually entrained, since some of the wax and essentially all of the oil is soluble in the test solvent. Alternatively, for higher temperature distillation fractions, comprising high molecular weight species, the ASTM tests are likely to report less oil than is actually entrained, since some of the oil and essentially all of the wax is insoluble in the test solvents. Thus, in general, the ASTM test methods do not report the correct amount of entrained oil in wax. Finally, the ASTM methods are time-consuming and require considerable operator skill in order to achieve the claimed precision, and are not amenable to on-line implementation.

Practical needs demand a method preferably for measuring the oil content of the wax, but which has general application to determining the content of a first constituent of a fluid mixture (following separation into that one constituent and at least one further constituent) either in the fluid mixture itself prior to the separation or in one or more further constituents.

Furthermore, the method should be suitable for on-line measurement or batch measurement, as circumstances require. A measurement method in which the need for dilution can be avoided and/or where rapid measurements can be made which can be used to control the separation process, is desirable.

SUMMARY OF THE INVENTION

As used herein, the terms "absorbance" and "absorptivity" will be defined as follows. Absorbance is defined as the logarithm of the ratio of the intensity of light incident on the sample to that transmitted through the sample. According to Beer's law, the absorbance of a medium can in general be expressed in a variety of ways, one of which is the product of the absorption coefficient or absorptivity and the optical pathlength through the medium. The absorptivity therefore, is the absorbance per unit length. The absorptivity, in turn may be expressed as the product of the absorption cross-section of the absorbing species and its concentration.

The present invention provides, in one aspect, a method for the spectroscopic determination of the amount $\alpha_{Nn}$ of the Nth constituent of a fluid mixture 0 in another constituent n of the mixture following the separation of said mixture into M, constituents 1,...,M (where n, $N \leq M$) and where, due to imperfect separation, said amount $\alpha_{Nn}$ of constituent N remains present with separated component n, said method comprising the steps of:

(i) determining the absorptivity $a_N$ of constituent N at a selected wavelength, or at multiple wavelengths across a selected wavelength range, in which constituent N exhibits light absorption;

(ii) determining the absorptivity $a_n$ of said another constituent n with said amount $\alpha_{Nn}$ of constituent N present at the same selected wavelength or at the same multiple wavelengths; and (iii) determining the amount $\alpha_{Nn}$ of said one constituent N present with constituent n from a mathematical expression which contains, or is equivalent to an expression which contains, the absorptivities $a_n$ and $a_N$ where the absorptivities are expressed solely as the ratio $a_n/a_N$.

"Equivalent" as used in the immediately preceding passage refers to the possibility of the mathematical expression used for determining $\alpha_{Nn}$ containing terms other than $a_n/a_N$ but which are equivalent. For example, the term $a_n/a_N$ could be replaced by the mathematically equivalent term $1/(a_N/a_n)$. Another example is the mathematical rearrangement of the terms in the mathematical expression, for example by bringing the term $a_n$ outside the remainder of the expression so that the terms within it include $1/a_n$. Another possibility is where the optical pathlength, $l$, used in the absorbance measurements is variable and set at a different magnitude for each absorbance measurement to yield the same measured absorbance value in both cases, so that $\alpha_{Nn}$ can be determined from an expression containing the ratio of the optical pathlength for constituent N to that for constituent n. This ratio, according to Beer's law, is equivalent to the ratio $a_n/a_N$ for the same optical pathlength used in the determination of both absorptivities $a_n$ and $a_N$. "Equivalent" is used correspondingly in the case of another ratio $a_0/a_N$ referred to in more detail hereinbelow. In other words, in all cases $\alpha_{Nn}$ is determined from a mathematical expression in which the absorptivities $a_n$ and $A_N$ are expressable solely as the ratio of $a_n/A_N$.

The present invention provides, in another aspect, a method for the spectroscopic determination of the amount $\alpha_{N0}$ of one constituent N of a fluid mixture 0 in that mixture following the separation of said mixture into M constituents $1,...,M$, (where $N \leq M$), said method comprising the steps of:

(i) determining the absorptivity $a_N$ of constituent N at a selected wavelength, or at multiple wavelengths across a selected wavelength range, in which constituent N exhibits light absorption;

(ii) determining the absorptivity $a_0$ of the fluid mixture prior to the separation, at the same selected wavelength or at the same multiple wavelengths; and (iii) determining the amount $\alpha_{N0}$ of said one constituent N in the fluid mixture 0 from a mathematical expression which contains, or is equivalent to an expression which contains, the absorptivities $a_0$ and $a_N$ where the absorptivities $a_0$ and $a_N$ are expressed solely as the ratio $a_0/a_N$.

In the case that the absorptivities are determined at a single selected wavelength, the mathematical expression may be used to compute the amount of constituent N in constituent n, as indicated above.

However, it is known that intrinsic absorption by constituent n, impurity absorption and/or scattering, instrumental noise, and baseline shifts may result in wavelength-dependent effects that contribute to the measured absorbance spectra. Measurement of the absorbance at multiple wavelengths in the selected wavelength range allows least square and other methods to be applied to obtain the value of the ratio of absorptivities which gives rise to the most accurate value of the amount of constituent N present in constituent n.

It will be shown mathematically hereinbelow that the entrained content $\alpha_{Nn}$ (or $\alpha_{N0}$) of constituent N in constituent n or feed 0 is a function of the quotient $a_n/a_N$ (or $a_0$ to $a_N$) or an equivalent expression. It follows that if only constituent N exhibits light absorbance at the selected wavelength or within the selected wavelength range and if the separation process does not alter the fundamental molecular absorption cross-section of constituent N but only its amount, the method is insensitive to changes in feed variability or upstream process conditions since the scale factor which involves the absorption cross-section and which relates the amount of constituent N to the absorptivity of the n, N, or 0 constituents is the same in the numerator and denominator of the ratio $a_n/a_N$ and $a_0/a_N$. It will be shown hereinbelow that the same is true even where light absorbing molecular contaminants are present and/or scattering is produced by dispersed phase present and/or one or more of the constituents other than constituent N also has absorbing properties at the selected wavelength or in the selected multiple wavelengths, providing the measured absorbances are corrected for the effect of these additional light absorbances or scattering. It follows that a change in the composition of the fluid mixture prior to the separation or (for example in the case of a waxy feed produced from a petroleum distillation column) a change in the upstream processing conditions, will not necessitate any recalibration.

As will be explained below, the invention is based on the assumption that Beer's law applies. Beer's law generally is obeyed by a wide range of absorbing species in dilute solutions, but deviations from linearity typically occur as the concentration increases due, for example, to increasing intermolecular interactions. However, the applicants have determined experimentally that, quite unexpectedly, the absorbance of dewaxed oil does not deviate from the linearity of Beer's law even at high oil concentrations.

Therefore, for the whole range of concentrations of oil in the wax likely to be measured, the measurement of oil content will remain very accurate. For other media for which Beer's law only applies at low concentrations, the spectroscopic methods disclosed herein should only be used for suitably low concentrations. For measurements at higher concentrations, preferably non-absorbing diluent or solvent should be added, to remain within the linear range of the equipment.

Reference has been made above to correcting the measured absorptivities for the effects of contaminating species, light scattering or other absorbing constituents. The correction may be done by modelling the effect, using a mathematical function such as polynomial or exponential functions of wavelength and determining the coefficients of the polynomial by known mathematical procedures such as linear regression analysis.

For determining the oil content of wax from a dewaxing process, the wavelength range for the absorbance measurement may be 250 nm to 650 nm, more preferably 316 to 500 nm and even more preferably 316 to 450 nm. The shortest wavelength of the range over which the absorbance measurements are made may be selected as that for which the measured absorbances are all within the upper limit of linearity of the equipment. Typically, 316 nm typically represents the shortest wavelength at which the need for diluting the oil and wax to remain within linear operation does not arise for a pathlength of 2 mm. The longest wavelength in this range is chosen to be that for which the measured absorbances are greater than a value representing noise in the equipment and is typically in the range from 400 to 500 nm. Because absorbance is a logarithmic function of the ratio of light intensity incident upon the absorbing medium to the light intensity transmitted through the absorbing medium, a very large dynamic range may be required of the detector/amplifiers/electronics in the absorbance-measuring equipment.

In practice, there may be instances where it is desired to limit the range of measured intensities. In order to accommodate measurement over the wavelength range, the pathlength can be varied until the measured absorbances of the one constituent N and other constituent n (containing a quantity of constituent N) are the same, the amount then being determined from the ratio of the respective pathlengths.

The invention relates not only to the novel and inventive method defined hereinabove, but also to apparatus for measuring the amount of constituent N in product constituent n. According then to another aspect of the invention there is provided apparatus for the spectroscopic determination of the amount $a_{Nn}$ of one constituent N of a fluid mixture 0 in another constituent n of the mixture following the separation of said mixture into said constituents 1,...,M (where n, N≦M) and where, due to imperfect separation, said amount $a_{Nn}$ of constituent N remains present with separated constituent n, said apparatus comprising:

(i) means arranged to determine the absorptivity $a_N$ of said one constituent N at a selected wavelength, or at multiple wavelengths across a selected wavelength range, in which constituent N exhibits light absorption and arranged also to determine the absorptivity $a_n$ of said another constituent n with said amount $a_{Nn}$ of constituent N present at the same selected wavelength or at the same multiple wavelengths; and (ii) computer means arranged to compute the amount $a_{Nn}$ of said one constituent N present with constituent n from a mathematical expression which contains, or is equivalent to an expression which contains, the absorptivities $a_n$ and $a_N$ where the absorptivities are expressed solely as the ratio $a_n/a_N$.

Alternatively the apparatus may be modified so that the absorptivity determining means determines the absorptivity $a_0$ of the fluid mixture 0 and $a_N$ and the computer means computes the content $a_{N0}$ of constituent N in fluid mixture 0.

In either case the computer means may additionally be arranged to control the separation process in dependence on the computed content $a_{Nn}$ (or $a_{N0}$), so as to minimize variations between the calculated value of $a_{Nn}$ (or $a_{N0}$) and a desired value for $a_{Nn}$ (or $a_{N0}$). Alternatively where $a_{N0}$ is determined, the determined amount may be used to control one or more parameters of the upstream process producing the fluid mixture 0, so as to minimize differences between the determined amount $a_{N0}$ and a desired value for this amount. Another possibility is to use $a_{N0}$ to divert, blend or further process the feed prior to the separation if the determined amount $a_{N0}$ differs from a desired value by more than a predetermined amount. This latter mode of operation would be appropriate, for example in the case where the separation process employs a catalyst which would otherwise quickly become poisoned by constituent N if it were present in the fluid mixture 0 in an excess of a predetermined amount.

In addition, the computer means may be programmed to provide a signal to an operator or process control computer in the event that the determined amount of constituent N in the feed or in a separated constituent n exceeds a predetermined target value, so that the operator or computer may select various processing options. For example, if the separation process involves a feed or a separated constituent n being acted upon by a catalyst or membrane and it has been determined that a critical amount of constituent N can reduce the lifetime or performance of the catalyst or membrane, then the determined value of $a_{N0}$ or $a_{Nn}$ may be used to determine when the amount of constituent N in the feed approaches or exceeds the critical amount so that the feed or separated constituent n can be blended or processed further before contacting the catalyst or membrane, or be diverted from the separation process.

In order to make absorbance measurements on a plurality of the product constituents, it is preferred to use a single spectrometer and either to repeatedly and sequentially flow the constituents through a spectrometer, for example using appropriate flow control valving operated under computer control, or to use fiber-optic probes to transmit light which has passed through the constituents to the spectrometer in which the light is then repeatedly and sequentially measured. The probes can be located either directly in the main product lines or in slip streams from those lines.

It will be appreciated that the method disclosed herein is suitable where batch separation is effected or for on-line use.

The foregoing and other description and features will now be described in greater detail.

BRIEF DESCRIPTION OF THE DRAWINGS

For a better understanding of the invention and to show how the same may be carried into effect, reference will now be made, by way of example, to the accompanying drawings, wherein:

FIG. 3 illustrates the spectra of a particular dewaxed oil and the corresponding wax, both of which were obtained from dewaxing the same feed, and a model for absorbing impurities, together with the corrected wax spectrum based on the model;

FIG. 8 shows the relationship between the entrained oil content of waxes obtained by the present method and that obtained from tests specified by the American Society of Testing Materials, for five different viscosity grades.

GENERAL DESCRIPTION OF THE INVENTION

Figure 1:
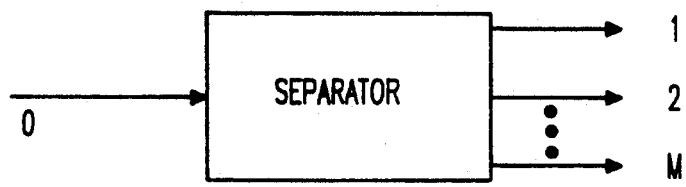
FIG. 1 very diagrammatically represents a separation process to which the novel measuring methods to be described hereinbelow can be applied.

FIG. 1 represents, very diagrammatically, a separation process which separates a fluid mixture feed 0 into M separated product constituents 1, 2,...,M. For example, the feed 0 could be a waxy raffinate and the separated constituents 1,2 would then be essentially wax and dewaxed oil (DWO), respectively.

Ideally, each separate output constituent 1,2,...,M from the separation process consists solely of that one constituent. However, in practice, no separation process is perfect and, for example, an amount of one constituent N may be entrained in at least one of the other M−1 constituents. An obvious example is that the wax resulting from a dewaxing process will contain a residual quantity of entrained dewaxed oil. Another example in the petroleum industry is a distillation process where "bottoms" (i.e., material with the highest boiling point)

can be entrained in decreasing residual quantities in increasingly higher "sidestreams" (i.e., materials with lower boiling points). However, it is to be understood that the invention finds general application where one constituent is present in amounts in one or more other product constituents. It will now be demonstrated that the amount entrained in each product constituent can be determined solely from absorption measurements on the M product constituents.

Consider an element (mass $m_0$) of the feed mixture 0 which is separated by the separation process into the M constituents, each having mass $m_1, m_2, ..., m_M$. Accordingly $$m_0 = m_1 + m_2 + ... + m_M$$

An element of the nth constituent (the element having mass $\hat{m}_n$) of the M product constituents comprises molecules having mass $m_n$ and density $\rho_n$, and also a quantity of constituent N, having mass $m_{Nn}$ and density $\eta_N$. The quantity $\alpha_{Nn}$ expressed as a weight fraction of constituent N which is entrained in product constituent n is defined as $$\alpha_{Nn} = m_{Nn}/m_n \quad (1)$$

Thus $$m_n = \hat{m}_n + \alpha_{Nn} m_n \quad (2)$$

The volume $V_n$ of the nth constituent is equal to the sum of the volumes of the molecules of mass $m_n$ and molecules of mass $m_{Nn}$ of constituent N, so that $V_n$ can be expressed as $$V_n = \hat{m}_n/\rho_n + \alpha_{Nn} m_n/\rho_N \quad (3)$$

where, as defined above, $\rho_n$ and $\rho_N$ are the densities of the n and N species, respectively.

On substituting for $\hat{m}_n$ in equation (3) using equation (2) and then substituting for $m_n$ using equation (1), it can be shown that $$\alpha_{Nn} m_n/V_n = \alpha_{Nn} / \left[ \frac{(1-\alpha_{Nn})}{\rho_n} + (\alpha_{Nn}/\rho_N) \right] \quad (4)$$

The assumption is made in the following analysis that only constituent N is absorbing. In the case of the exemplified dewaxing of waxy feed, it is true to say that across the wavelength range having lower and upper limits approximately equal to 250 nm to 650 nm, more preferably 316 nm to 500 nm and even more preferably 316 nm to 450 nm, any absorbance by the wax itself is negligible, so that the absorption exhibited by the wax is due solely to the entrained oil content. Where one or more of the other constituents does exhibit absorption at the selected wavelength or within the selected wavelength range, it may be possible to correct for this, as described in some detail hereinbelow.

Figure 2:
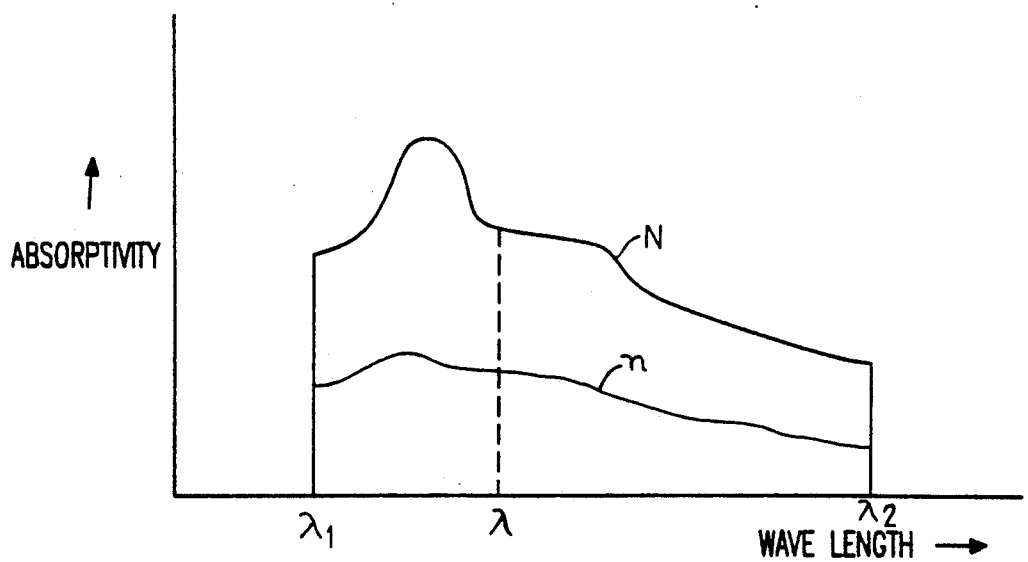
FIG. 2 illustrates the absorbance spectra of the nth and Nth product constituents from a separation process where an amount of constituent N is present in the nth product constituent an constituent N exhibits absorbance across selected wavelength range but constituent n is such that, in the absence of constituent N, it would not.

FIG. 2 illustrates, diagrammatically, the absorbance spectrum (N) of a medium across a wavelength range (lower and upper limits $\lambda_1$ and $\lambda_2$) in which that medium exhibits absorption and that (n) of product constituent n which is due solely to the entrained content of constituent N because constituent n itself is non-absorbing. The amount of constituent N in product constituent n is lower than that in product constituent N, so that the magnitude of the absorptivity at any wavelength of constituent n is lower than that of constituent N and the ratio of absorptivity at any wavelength $\lambda$ between $\lambda_1$ and $\lambda_2$ is ideally independent of wavelength and is constant.

From the foregoing, it follows that the absorbances $A_n$ and $A_N$ of the nth and Nth constituents are expressed as $$A_n = (N_{Nn}/V_n)\epsilon_N l_n$$

$$A_N = (N_N/V_N)\epsilon_N l_N$$

where $N_{Nn}$ and $N_N$ are the numbers of absorbing molecules of constituent N in constituents n and N in volume elements $V_n$ and $V_N$, respectively (so that the concentrations of constituent N in product constituents n and N are $(N_{Nn}/V_n)$ and $(N_N/V_N)$, respectively), $\epsilon_N$ is the absorption cross-section per molecule of constituent N, and $l_n$ and $l_N$ are the optical pathlengths through constituents n and N, respectively.

$A_n$ and $A_N$ can then be expressed as $$A_n = (m_{Nn}/V_n) \cdot \epsilon_N N_A l_n / MW_N,$$

and $$A_N = \rho_N \cdot \epsilon_N N_A l_N / MW_N,$$

since $N_{Nn} = m_{Nn} \cdot N_A / MW_N$, where $N_A$ is Avogadro's number and $MW_N$ is the molecular weight of constituent N, $N_N = m_N \cdot N_A / MW_N$, where $m_N$ is the mass of constituent N in product constituent N, and $m_N/V_N = \rho_N$.

From equation (1) $m_{Nn} = \alpha_{Nn} m_n$, so that the absorptivities $a_n$, $a_N$ of the nth and Nth constituents, defined as $A_n/l_n$ and $A_N/l_N$, respectively can be expressed as $$a_n = A_n/l_n = (\alpha_{Nn} m_n/V_n)\epsilon_N N_A/MW_N,$$

and $$a_N = A_N/l_N = \rho_N \epsilon_N N_A/MW_N$$

Defining $R_{nN} (= a_n/a_N)$ as the ratio of the absorptivity of the nth constituent to the Nth constituent, it follows that $$\alpha_{Nn} m_n/V_n = \rho_N R_{nN} \quad (5)$$

Equating (4) and (5) and solving for $\alpha_{Nn}$ it follows that $$\boxed{\alpha_{Nn} = \frac{(\rho_N/\rho_n) \cdot R_{nN}}{1 + R_{nN}(\rho_N/\rho_n - 1)}}$$

Expressed in words, this equation shows that the amount expressed as a weight fraction $\alpha_{Nn}$ of constituent N in product constituent n is a function solely of the ratio of the absorptivity of the constituent n to that of the constituent N and the density ratio $\rho_N/\rho_n$ of the constituents N, n, respectively.

It follows that the content of the constituent N can be measured spectroscopically under on-line conditions, using the method disclosed herein. Of course, the method could alternatively be used for batch measurement, where a given quantity of fluid mixture is separated into respective quantities of its product constituents and the spectroscopic measurements then performed, from which the weight fraction $a_{Nn}$ can be calculated. Conveniently, the calculation is performed by a computer into which constituent density data are entered and which receives measured absorbance data, from which the amount of constituent N in one or more of the other M−1 constituents is computed. Conveniently the computer can provide a digital or visual output display of the residual content output data.

A particular advantage of the measuring method disclosed herein is that changes in the composition of the fluid mixture feed or any upstream processing conditions affecting the absorptivity of constituent N will correspondingly change the absorptivity of constituent n because constituent n itself is assumed not to have light absorbing properties at the selected operating wavelength or within the selected wavelength band or can be corrected for any such absorption and because the absorptivity exhibited by constituent n is due solely to the absorbance of the amount of constituent N in product constituent n. It follows that the value of the ratio $R_{nN}$ is unchanged and, importantly, this means that no recalibration is required.

In the particular case of dewaxing in waxy raffinates for example, the product constituents are wax and DWO, M=2, and the wax and DWO could be regarded as product constituents 1 and 2, respectively, with densities $\rho_w$ and $\rho_o$, respectively, and the ratio of the measured wax absorptivity to measured oil absorptivity $R_{wo}$ (=$R_{12}$). It would follow that $a_{ow}$(=$a_{21}$) would be computed from the formula:

$$a_{ow} = \frac{(\rho_o/\rho_w)R_{wo}}{1 + R_{wo}(\rho_o/\rho_w - 1)} \tag{6}$$

As indicated above a modification involves determining the absorptivity $a_{N0}$ of the feed 0 and computing the content of constituent N in feed 0 from a mathematical formula including the term $R_{0N}$ where $R_{0N}=a_0/a_N$. By applying a mathematical analysis similar to that set out above, it can be shown in a straight forward manner that $a_{N0}$ is given by the formula $$\boxed{a_{N0} = (\rho_N/\rho_0) \cdot R_{0N}}$$

where $\rho_0$ is the density of the feed.

The description given above relates to the situation where only the constituent N which is present, due to imperfect separation process, in the other M−1 product constituents, exhibits absorption at the selected wavelength or at multiple wavelengths across the selected wavelength range. These circumstances will apply, at least to a large extent, in a number of practical situations. Indeed, in the case of the dewaxing of waxy raffinate, the wax has negligible absorption in a wavelength range whose lower and upper limits are approximately 250 to 650 nm, as mentioned above. However, where one or more other constituents are absorbing and/or contain absorbing contaminants and/or scattering is produced by dispersed phase present, the measured absorbance spectra will be distorted by these effects. In order to overcome inaccuracies in the determined amount due to such effects, the effects can be modelled and the measured absorbance spectra corrected accordingly. The modelling may be based on a polynomial or exponential function of wavelength and the coefficients determined from known mathematical techniques such as linear regression analysis. Other models may be developed and the necessary calculations made. Such techniques do not form part of the invention as such and are well known in the art, and so need to be further described herein. However, by way of example, a specific example of modelling, and correcting for, the contributed spectrum produced by an absorbing contaminant or by scattering due to dispersed phase present, by a quadratic function of wavelength will be described in some detail hereinbelow. Alternatively, if the absorbance spectrum of absorbing constituent n (in the absence of constituent N) or that due to absorbing contaminants and/or scattering is known or may be determined, the measured absorbance of constituent n in the presence of constituent N and any contaminants present may be corrected in accordance with this contributed spectrum.

Figure 3:
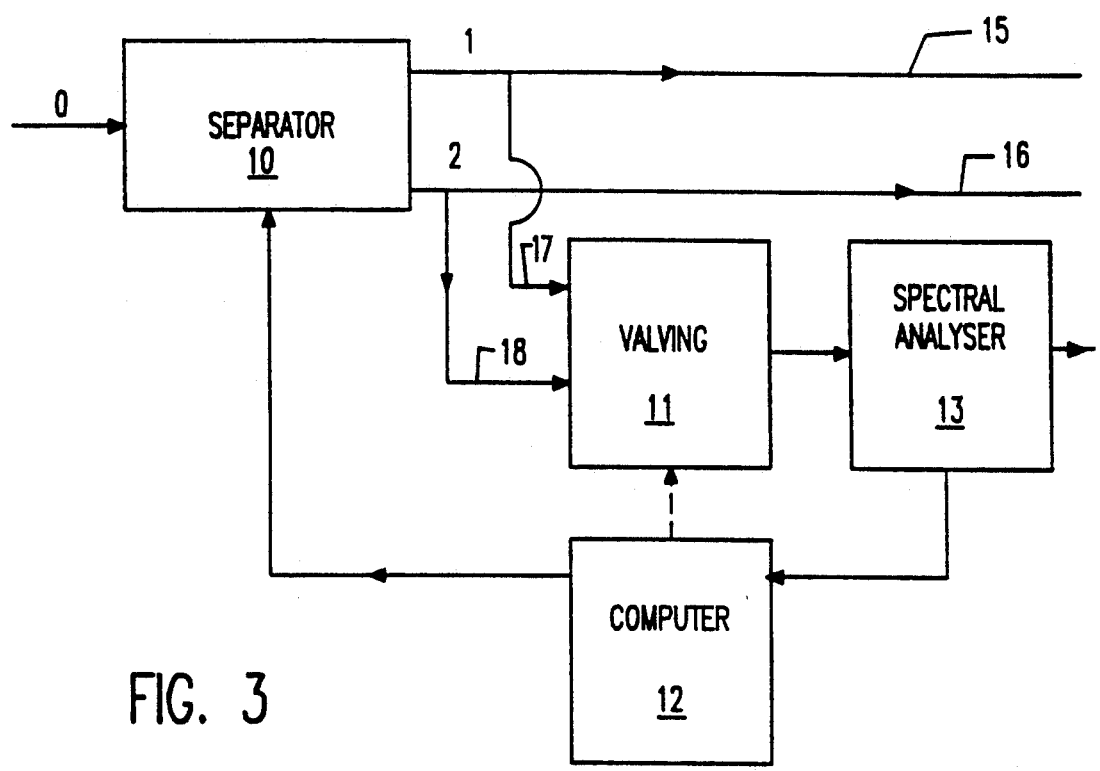
FIGS. 3 and 4 are schematic block diagrams of two forms of equipment in accordance with the invention which are suitable for performing the spectroscopic measurement of the amount of a constituent 2 in another product constituent 1, and optionally the control of the separation process in order that variations from a desired amount are minimized.

Referring now to FIG. 3, there is shown, schematically, one form of equipment suitable for performing the inventive method on-line. The fluid mixture feed 0 is separated in separator 10 into two constituents 1, 2, in product lines 15, 16, respectively. Successive quantities of product constituents 1, 2 from sidestreams 17, 18 of product lines 15, 16 respectively, are fed, though appropriate valving 11 under operation by a computer system 12, alternatively and sequentially through a spectral analyzer 13 which includes a spectrometer which performs the required absorption measurements and supplies its output data to system 12. The constituent leaving the spectral analyzer 13 is then discharged to waste or (if the constituent has sufficient value) returned, by further valving (not shown), also under control by the computer system 12, to line 15 (constituent 1) or line 16 (constituent 2). The computer system 12 calculates the amount $a_{21}$ of constituent 2 from the output data received from the spectral analyzer 13, compares the result with a desired value for the amount $a_{21}$, and controls one or more parameters of the separation performed in separator 10, so as to minimize any difference between the calculated content and the desired value. If the equipment is used solely for providing on-line monitoring of the content of the constituent 2, then computer control of the separation process is not required and the computer system merely generates an output indication (e.g., an alarm, a visual display or a printout) of the calculated amount $a_{21}$.

Figure 4:
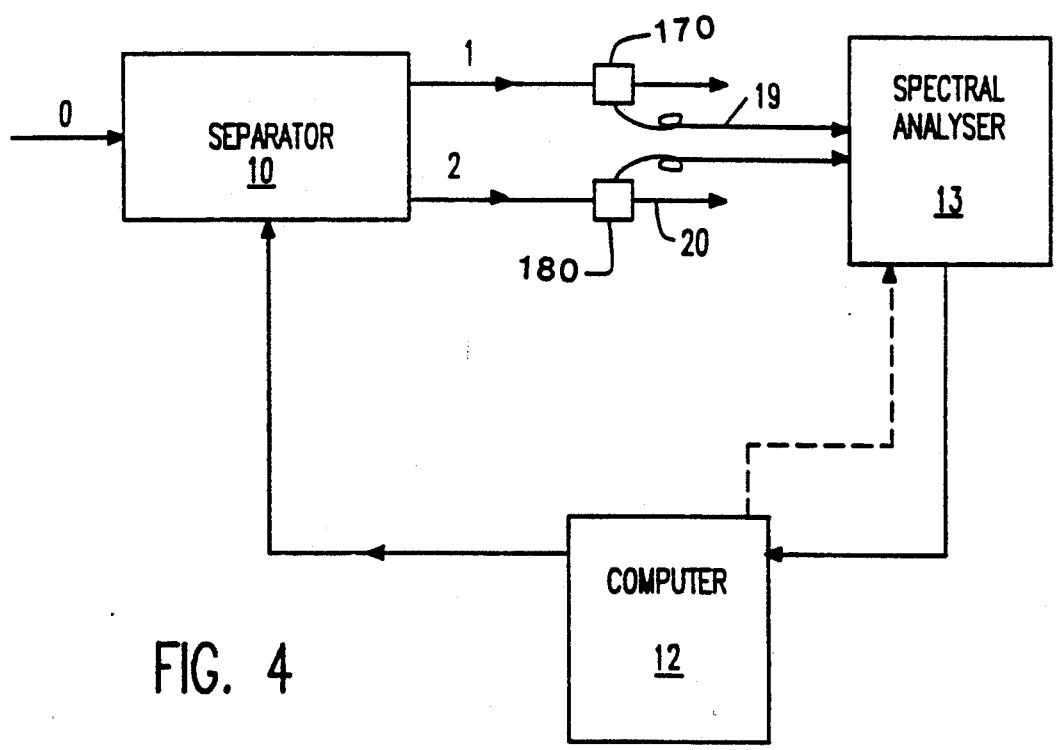

A modification is shown in FIG. 4 where fiber-optic probes 170, 180 which as shown, are inserted in the product lines of constituents 1, 2, respectively (or in slipstreams, derived from these product lines), receive the light intensity which has passed through fiber-optic cables 19, 20, to spectrometer 13 which alternately samples the intensity of light from the fiber-optic cables. The computerized management system 12 responds to the output data from spectral analyzer 13 in exactly the same way as in the FIG. 3 embodiment, whether to provide an output indication of the amount $a_{21}$ or to control the operation of the separation process.

The FIGS. 3 and 4 embodiments are used where the separator provides only two product constituents 1, 2 and the absorptivity measurements are performed on those two constituents. It will be readily apparent to the skilled reader, however, how to adapt the equipment where the feed 0 is separated into more than two product constituents and further description of this, therefore, will not be given. Where $a_{N0}$ is to be determined, either a slipstream is taken from feed 0 to the spectrometer (rather than from product line 15) or a fiber-optic link is used between a fiber-optic probe, through which the feed 0 passes or which is positioned in a slipstream from the feed 0, and the spectral analyzer.

DETAILED DESCRIPTION OF PREFERRED EMBODIMENTS

A preferred way of performing the invention will now be described. The wax absorbance should be measured at elevated temperature, typically at 60°-120° C., more preferably 70°-110° C., where the wax and entrained oil comprise a single, miscible phase. The temperature value is not critical but should be chosen to be greater than the temperature at which the wax melts and less than the temperature which causes degradation of the wax or other operational difficulties. Operation at these conditions minimizes fluctuations in the measurements due to absorption inhomogeneities and to scattering by immiscible components. Hot filtration of the wax may be required if scale or other particulates are present which can cause significant scattering of the light.

Absorbance measurements on the dewaxed oil are made at the same, or nearly the same temperature as for the wax. This minimizes errors in the density ratio of the oil and wax which is used in the equation relating the absorbance ratio to the wt % of entrained oil. It also ensures that the absorbance of the oil, which may be temperature sensitive, is the same in both constituents by keeping the temperature substantially the same.

Both the wax and dewaxed oil samples may need to be diluted in order to measure their absorbances in optical cells of convenient pathlength. White oils such as Isopar H (a high purity isoparaffinic solvent with a narrow boiling range and low aromatics level made by the Exxon Company U.S.A.) are ideal diluents, since they exhibit low absorption in the measurement wavelength range, are non-volatile at the measurement temperature, are chemically inert and are miscible with both the molten wax and the dewaxed oil.

The same white oil should also be used as a reference. Reference measurements should be made in the same pathlengths as used for the wax and dewaxed oil measurements. Dilution and optical pathlengths may be chosen to adjust the measured absorbances to be significantly above the noise level yet remain within the range of linear response of the instrument.

The wt % of oil in the wax sample, $\alpha_{ow}$ may be calculated from the measured absorbance of the wax and dewaxed oil by $$\alpha_{ow} = R_{wo} K_1 / \{K_2 - R_{wo} K_3\} \quad (7)$$

where
$R_{wo} = a_w / a_o$
$a_w$ = absorptivity of the wax ($=A_w/l_w$, where $A_w$ is the measured absorbance of the wax and $l_w$ is the optical pathlength through the wax)
$a_o$ = absorptivity of the oil ($=A_o/l_o$, where $A_o$ is the measured absorbance of the dewaxed oil and $l_o$ is the optical pathlength through the oil).
$K_1 = \{Z_{ow} + (W_{sw}/W_w)Z_{os}\}$
$K_2 = \{1 + (W_{so}/W_o)Z_{os}\}$
$K_3 = (1 - Z_{ow})$
and where
$Z_{ow}$ = ratio of oil density to wax density
$Z_{os}$ = ratio of oil density to solvent density
$W_{sw}$ = weight of solvent added to dilute wax sample
$W_w$ = weight of wax sample
$W_{so}$ = weight of solvent added to dilute dewaxed oil sample
$W_o$ = weight of oil sample The wax absorbance which is used in the above formula is preferably corrected for the absorption and scattering by components of the wax other than the dewaxed oil. The corrected wax spectrum is obtained by the following method.

The measured wax absorbance is considered to be due to the sum of two effects. The first is the absorption by the entrained dewaxed oil. This spectrum is identical to that measured for the dewaxed oil except for a scale factor, K (where K<1). Consequently, the entrained oil contributes the absorbance spectrum, $KA_o$ to the measured wax spectrum.

The second effect, absorption by molecular contaminants, such as asphaltenes, and/or scattering by an unwanted dispersed phase, contributes the spectrum, B, to the measured wax spectrum. We have found that this spectrum may be approximated by a quadratic function of the wavelength, $\lambda$, as $$B = B_0 + B_1 \lambda + B_2 \lambda^2$$

over the selected wavelength range.
Thus, the measured wax absorbance $A_w$ can be expressed as $$A_w = KA_o + B_0 + B_1 \lambda + B_2 \lambda^2$$

The coefficients, $K$, $B_0$, $B_1$, and $B_2$, are obtained by a least squares regression of the measured wax spectrum, $A_w$ to $A_o$, the measured dewaxed oil spectrum, $\lambda$, and $\lambda^2$. The corrected wax spectrum is the product of the regression coefficient, K, and the dewaxed oil spectrum, $A_o$. Consequently, the ratio ($A_w/A_o$) reduces simply to the regression coefficient, K, and equation (7) becomes $$\alpha_{ow} = R_{wo} K_1 / (K_2 - R_{wo} K_3)$$

where $R_{wo} = K(l_o/l_w)$.

A preferred wavelength range for the method is 316–450 mm. The pathlength and dilutions are chosen to give absorbance levels between 3.0 and 0.002 AU (AU=absorbance units), more preferably 2.2 and 0.02 AU and even more preferably 2 and 0.05 AU.

Figure 5:
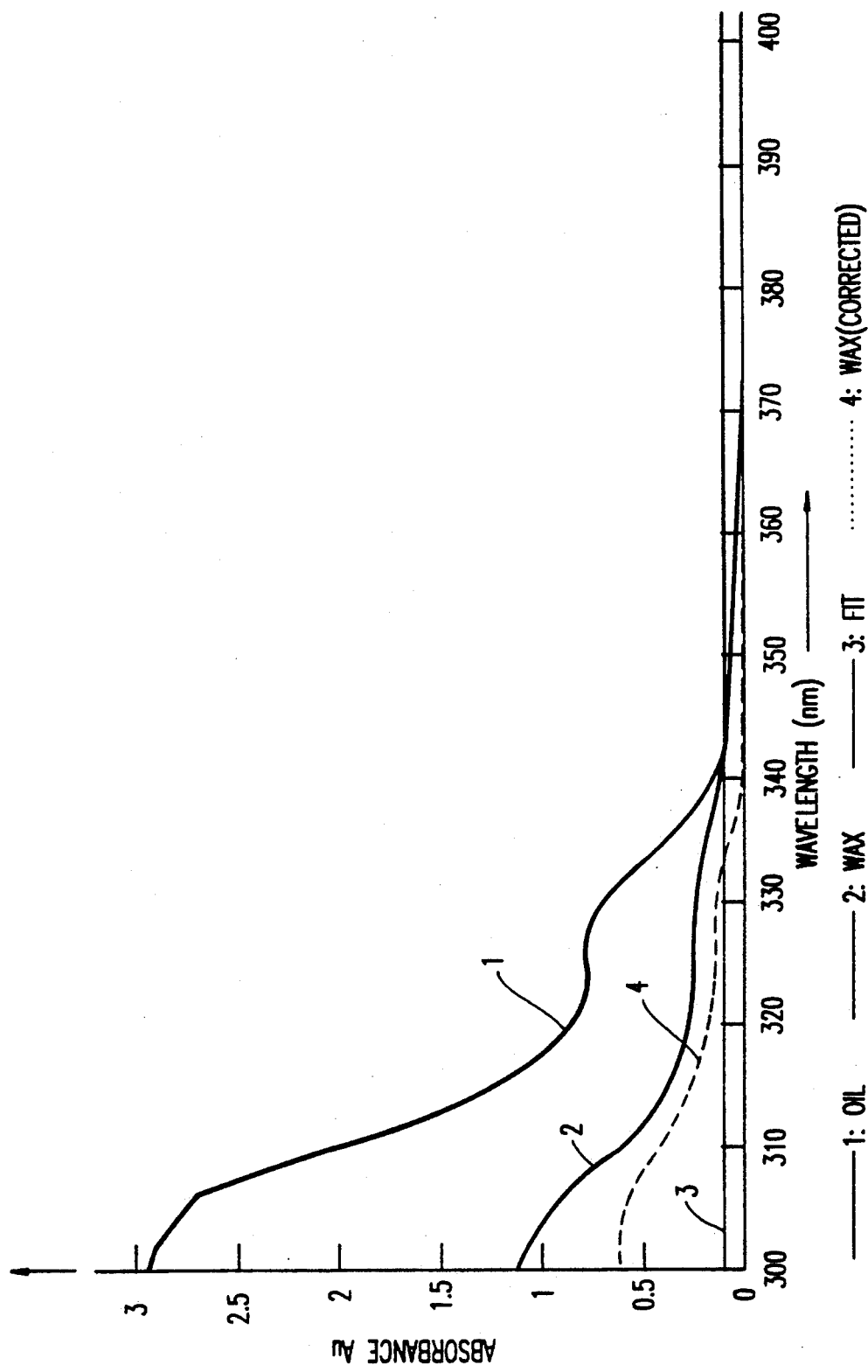

The spectra of a dewaxed oil (coded BR 150N, and obtained from Exxon Company, U.S.A., Baton Rouge refinery, having ISO viscosity grade of 150) and the wax derived from the same feed as that oil, containing 0.4% oil and which is contaminated by absorbing impurities are shown as curves 1 and 2 in FIG. 5. Curve 3 is the function, B, which is quadratic in wavelength and best approximates the contaminant absorbance and where coefficients $B_0$, $B_1$ and $B_2$ (together with coefficient K) are obtained from a least squares linear regression analysis. The corrected spectrum of the wax, which is obtained by multiplying the measured oil spectrum $A_o$ by the determined value of coefficient K, is shown as curve 4. This spectrum differs from the dewaxed oil spectrum only by the scale factor K which, in this case, represents an entrained oil content of 0.4 wt %.

Figure 6:
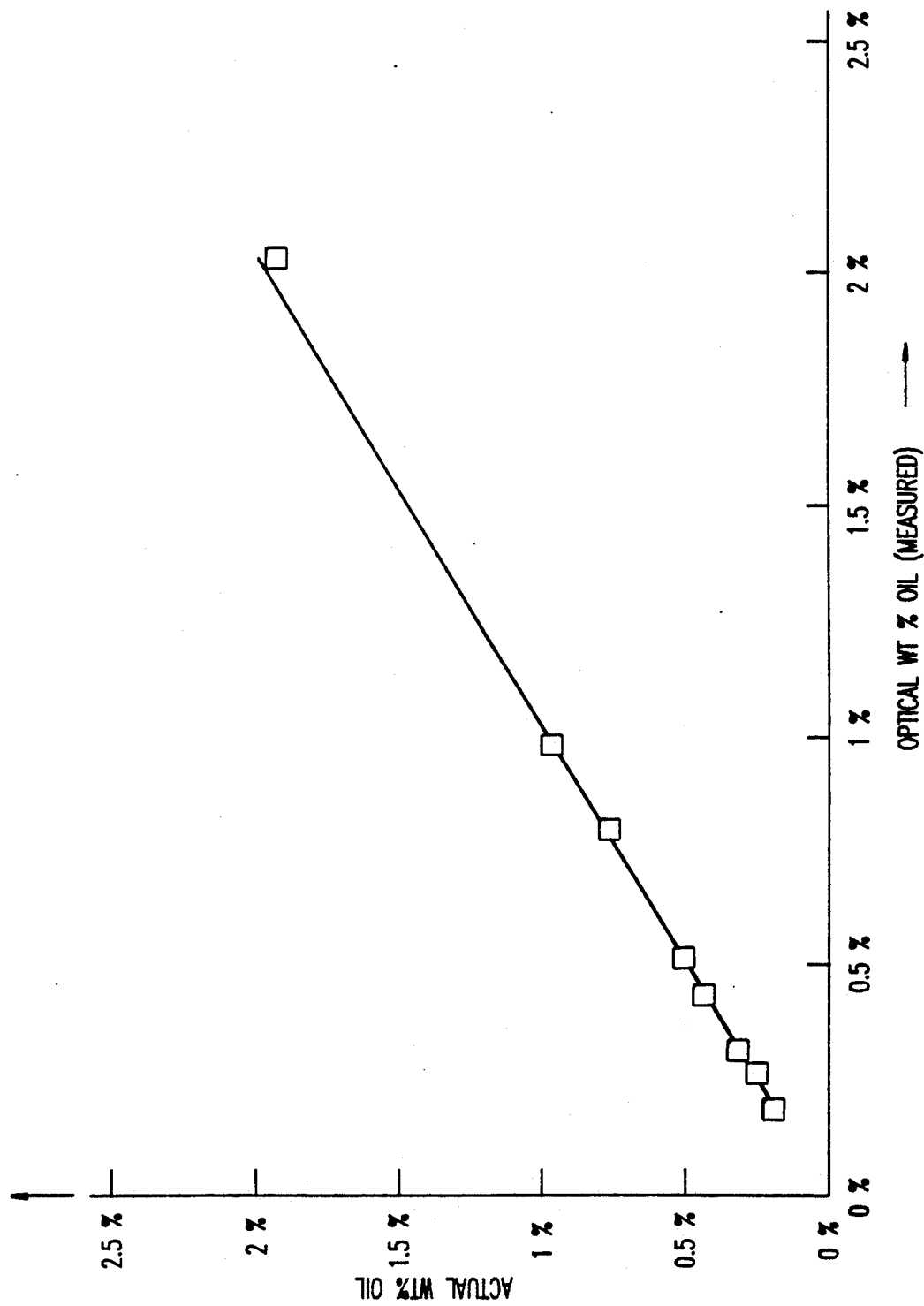
FIGS. 6 and 7 indicate the accuracy and linearity of the content measurements made by the present spectroscopic method.
Figure 7:
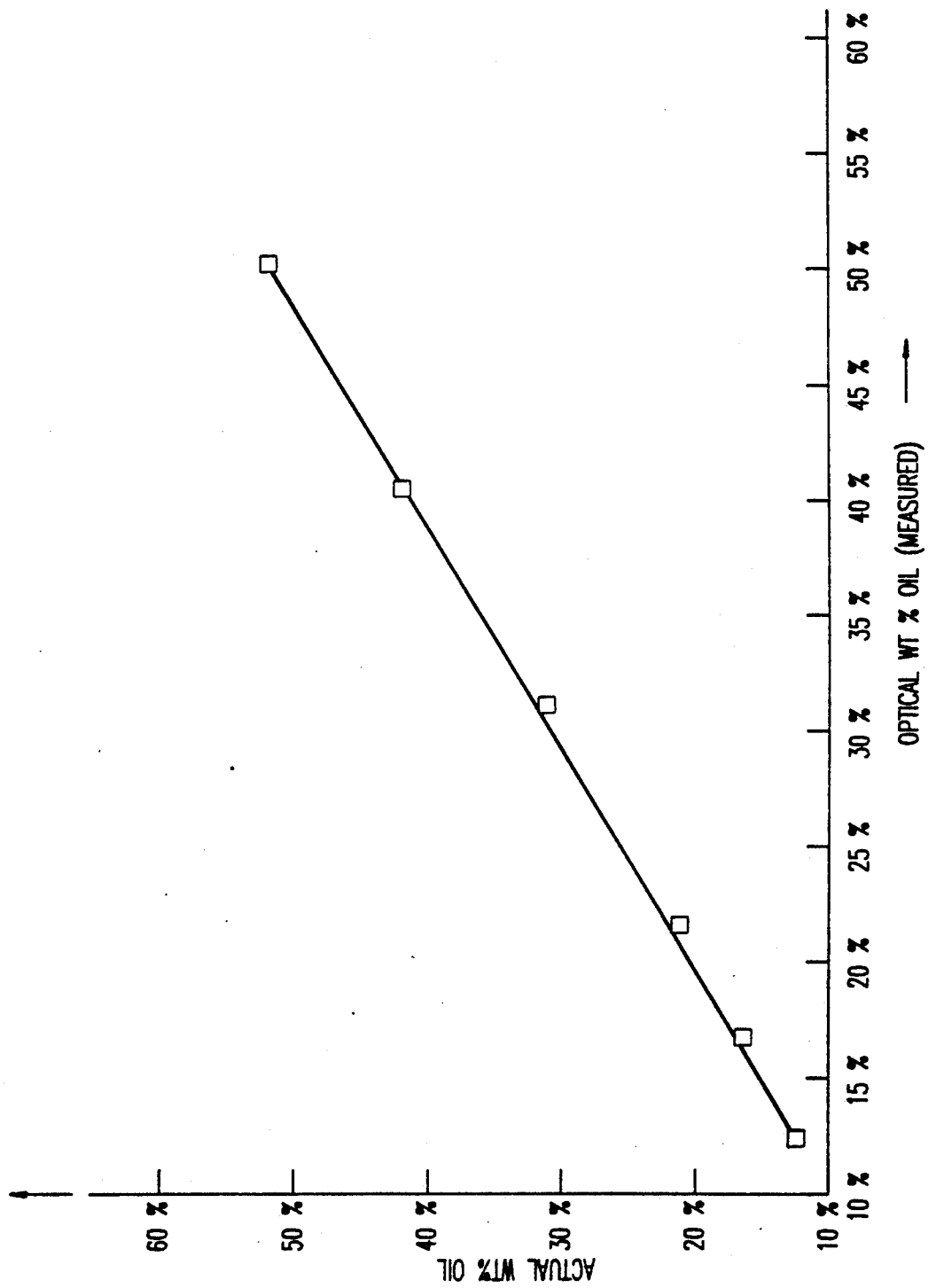

The accuracy of the method for measuring entrained oil content is shown in FIGS. 6 and 7. Oil (coded BR 100N and BT 600N) obtained from Exxon Company, U.S.A., Baton Rouge and Baytown refineries, respectively, and having respective ISO viscosity grades of 100 and 600) was added back to plant wax samples derived from those oils, respectively. It was assumed that the optical method gave the correct oil content for the "as received" wax. Known additions of dewaxed oil resulted in values for the actual wt % oil which is plotted on the ordinate of each graph. It can be seen that the method is accurate over the range of 0.2% to 50% entrained oil.

The precision of the method was demonstrated by repeat measurements made by different operators in different laboratories. The measured standard deviation for the optical method compares favorably with, and is usually superior to, the claimed standard deviation for the ASTM tests. The measurement time for the optical method is less than 10 minutes, while the ASTM tests take approximately an hour to perform.

With reference to FIG. 8, entrained oil content of waxes, obtained by the optical method, is related to the solvent extractable wax content, obtained by the ASTM test D 3235. This relationship differs with viscosity grade but is independent of feed or process changes. The ASTM wt % oil versus that predicted from the last described optical method is shown in FIG. 8 for five viscosity grades, MCT-5, 10, 20, 30, and 60, (lubricating oils designated by MCT-5, MCT-10, MCT-20, MCT-30, MCT-60: "Medium cold test" lubricating oil basestocks having ISO viscosity grades of approximately 100, 150, 500, 600, and 850, respectively obtained from Imperial Oil Ltd) with standard errors of estimates of 0.41%, 0.12%, 3.13%, 1.36%, and 0.85%, respectively.

The present method provides a simple and fast laboratory procedure, and should result in a reliable optical oil-in-wax analyzer for on-line applications.

A preferred way of operating the equipment will now be described, in which the following steps are carried out.

Measure separately, the absorbance spectra of the oil, $A_o$, and wax, $A_w$, without dilution in a 2 mm pathlength cell, over the wavelength range 316 to 500 nm.

Determine a wavelength, $\lambda_1$, as the minimum wavelength in this range for which both the oil and wax absorbances are <2.2 AU (absorbance units), where this value of 2.2 AU is selected as defining the approximate upper limit of the linear range of the instrument.

Determine a wavelength $\lambda_2$ as the maximum wavelength in this range for which both the oil and wax absorbances are >0.01 AU, where this value is chosen as exceeding the approximate maximum level of noise in the equipment by at least a factor of 5.

Over the wavelength range $\{\lambda_1, \lambda_2\}$, fit the wax absorbance spectrum to the function $KA_o + B_0 + B_1\lambda + B_2\lambda^2$; where $\lambda$ is the wavelength, and K, $B_0$, $B_1$ and $B_2$ are coefficients to be determined by a least-squares criterion.

As in the original method, the wt % oil in wax is calculated from K and the oil and wax pathlengths and densities, as in equation (7).

The spectrometer used for measuring the absorbances may be operated under microcomputer control, in which the microcomputer can be programmed to determine $\lambda_1$ and $\lambda_2$ for each oil/wax pair once their spectra are measured. Thus, the regression range $\{\lambda_1, \lambda_2\}$ is optimally and automatically determined for each sample. This method of dynamic wavelength selection ensures that accurate absorbances for both the oil and wax are used in the determination of oil content.

Both the oil and wax may be measured undiluted, thereby eliminating the need for sample preparation (i.e., dilution) steps. This simplification has been found to reduce the total measurement time to approximately 5 minutes and minimizes errors due to inaccurate sample and/or diluent weighings.

Exactly the same method as originally demonstrated in the laboratory was incorporated into an on-line analyzer version using a process diode array spectrometer made by the Dupont company. Since the present method uses longer wavelengths, dynamically determined by the analyzer, the corresponding weaker specific absorbances permit the use of a longer path flow cell (say 2 mm) for both the oil and wax. This use of longer path flow cells minimizes the chances of plugging and the effects of film formation, resulting in a more reliable and accurate analyzer.

The detectors/amplifiers/electronics used in the spectroscopic equipment for making the absorptivity measurements may need to have a very large dynamic range. In practice though, cost, accuracy and the like may dictate that the operating range of the spectrometer be limited to, say, one decade, or similar. In order to maintain spectroscopic measurements over the same range of light intensities, the absorbance measuring apparatus may be equipped with some suitable arrangement for varying the optical pathlength and the absorptivity determinations made according to the following steps:

Choose a value for the minimum optical path length, $l_{min}$, for the oil which is practical for an on-line measurement (i.e., to avoid or minimize clogging up of the flow gap by particulate material). Typically, $l_{min} \geq 0.5$ mm.

Specify a maximum absorbance, $A_{max}$, which the instrument can determine quantitatively. $A_{max}$ must be a value which is below the maximum for which the instrumentation is within its linear operating range. Typically, $A_{max} \leq 3$.

For the dewaxed oil (DWO) of interest, determine the wavelength, $\lambda$, for which the absorbance, $A_{DWO}$, in a pathlength $l_{min}$, is equal to $A_{max}$.

Determine the optical pathlength $l$ in the wax for which the absorbance at wavelength $\lambda$ in the oily wax is $A_{max}$. The oil content of the wax is then given by equation (7), where $R_{wo} = l_{min}/l$.

It could happen that for a wax whose oil content is very small, the foregoing steps would need to be performed with the instrument operating in a domain where the noise level in the instrument becomes significant or dominant. In order to be able to measure such a low oil content accurately, for a wax with the minimum oil content of interest, $O_{min}$, the optical pathlength, $l_{max}$, should be determined, for which the absorbance $A_{min}$ at wavelength $\lambda$ is equal to a threshold absorbance, $A_t$. The threshold absorbance, $A_t$, is determined such that effects other than bulk intrinsic absorbance (e.g., scattering, refraction, etc.) are negligible. A typical value of $A_t$ is 0.02 AU. The maximum oil content which can be measured will then be $O_{min} \cdot (A_{max}/A_{min})$; or typically $150 \times O_{min}$. The equipment is then suitable for measuring oil contents between these maximum and minimum values only.

It is implicit in the description above that the intrinsic absorption properties of the absorbing species (i.e., constituent N) present at the time the absorbance measurements are made are preferably the same or, expressed another way, the absorbing species were mixed together in a common element of the feed 0 prior to the separation. The operation of the equipment preferably takes account of this consideration, which is more important when, for example, the flowrate of product constituent N is significantly different from that of product constituent n (or 0) whose absorbance is also being measured and/or when the composition of the feed is likely to change significantly with time.

It should be understood that the foregoing disclosure and description are only illustrative and explanatory of the invention. Various changes in and modifications to the elements of the inventive method and apparatus, as well as in the details of the disclosed method are apparatus, may be made within the scope of the appended claims without departing from the spirit of the invention.

What is claimed is:

1. A method of separating a fluid mixture 0 into M constituents 1,...,M and of spectroscopically determining the amount $\alpha_{Nn}$ of the Nth constituent of said fluid mixture 0 in another constituent n (where n, $N \leq M$) of the mixture where, due to imperfect separation, said amount $\alpha_{Nn}$ of constituent N remains present with separated constituent n, said method comprising the steps of:
   (i) performing the separation of the fluid mixture into its M constituents;
   (ii) passing light through constituent N;
   (iii) producing a first output representing the absorptivity $a_N$ of constituent N at at least one selected wavelength at which constituent N exhibits light absorption;
   (iv) passing light through constituent n;
   (v) producing a second output representing the absorptivity $a_n$ of said another constituent n with said amount $\alpha_{Nn}$ of constituent N present at the same at least one selected wavelength; and
   (vi) generating, from said first and second ouputs, a third output, said third output representing the amount $\alpha_{Nn}$ of said one constituent N present with constituent n, wherein
   (vii) the amount $\alpha_{Nn}$ of said one constituent N present with constituent n is determined in step (vi) from a mathematical expression in which the absorptivities $a_n$ and $a_N$ are expressable solely as the ratio $a_n/a_N$.

2. A method as claimed in claim 1 for the spectroscopic determination of the entrained oil content of wax resulting from the separation of a waxy raffinate into dewaxed hydrocarbon oil boiling in the lubricating oil range, wherein the oil amount, $\alpha_{ow}$, is determined in step (vi) as a weight fraction of the wax from the formula $$\alpha_{ow} = \frac{(\rho_o/w_\rho) R_{wo})}{1 + R_{wo}(\rho_o/\rho_w - 1)}$$

where o and w are the densities of the oil and wax respectively and $R_{wo}(=a_w/a_o)$ is the ratio of the absorptivities ($a_w$, $a_o$ respectively) of the wax and oil.

3. A method as claimed in claim 1 for the spectroscopic determination of the entrained oil content of wax resulting from the separation of a waxy raffinate into dewaxed hydrocarbon oil boiling in the lubricating oil range, wherein solvent is added to samples of the oil-bearing wax and the dewaxed oil before step (i) is performed and wherein the oil amount, $\alpha_{ow}$, expressed as a weight fraction of the wax is determined from the formula:

$$\alpha_{ow} = R_{wo}K_1/\{K_2 - K_{wo}K_3\}$$

where $R_{wo} = a_w/a_o$ $a_w$ = absorptivity of the wax ($=A_w/l_w$, where $A_w$ is the measured absorbance of the wax and $l_w$ is the optical pathlength through the wax)

$a_o$ = absorptivity of the oil ($=A_o/l_o$, where $A_o$ is the measured absorbance of the dewaxed oil and $l_o$ is the optical pathlength through the oil)

$K_1 = \{Z_{ow} + (W_{sw}/W_w)Z_{os}\}$ $K_2 = \{1 + (W_{so}/W_o)Z_{os}\}$ $K_3(1-Z_{ow})$ and where $Z_{ow}$ = ratio of oil density to wax density $Z_{os}$ = ratio of oil density to solvent density $W_{sw}$ = weight of solvent added to dilute wax sample $W_w$ = weight of wax sample $W_{so}$ = weight of solvent added to dilute dewaxed oil sample $W_o$ = weight of oil sample, and wherein the measured absorbance $A_w$ of the oil-bearing wax is corrected (to absorbance spectrum $KA_o$, where $K(<1)$ is a proportionally constant) for the absorbance spectrum contributed by at least one of the two physical effects selected from the group consisting of (i) absorption by molecular contaminants in the oil-bearing wax and (ii) scattering by dispersed phase present in the oil-bearing wax, said correction being made by determining the coefficients K, $B_o$, $B_1$ and $B_2$ of the formula $A_W = KA_o + B_o + B_1\lambda + B_2\lambda^2$ where $B_o + B_1\lambda + B_2\lambda^2$ approximates said contributed absorbance spectrum, by a least squares regression of the measured wax absorbance to $A_o$, $\lambda$ and $\lambda^2$ and by using the determined value of coefficient K to determine the oil amount, $\alpha_{ow}$, of the wax from said formula for $\alpha_{ow}$, where $r_{wo} = Kl_o l_w$, and $l_w$ being, respectively, the optical pathlengths through the dewaxed oil and wax.

4. A method as claimed in claim 2, wherein the wax absorbance $A_w$ (where $A_w = a_w \cdot l_w$ being the optical pathlength in the oil-bearing wax for the absorbance measurement of the oil-bearing wax) and the dewaxed oil absorbance $A_o$ (where $A_o = a_o \cdot l_o$, $l_o$ being the optical pathlength in the dewaxed oil for the absorbance measurement of the dewaxed oil) are measured and the absorbance $A_w$ of the oil-bearing wax is corrected (to absorbance spectrum $KA_o$, where $K(<1)$ is a proportionally constant) for the absorbance spectrum contributed by absorption by molecular contaminants in the oil-bearing wax and/or by scattering by dispersed phase present in the oil-bearing wax, said correction being made by determining the coefficients K, $B_o$, $B_1$ and $B_2$ of the formula $A_w = KA_o + B_o + B_1\lambda + B_2\lambda^2$ where $B_o + B_1\lambda + B_2\lambda^2$ approximate said contributed absorbance spectrum, by a least squares regression of the measured wax absorbance to $A_o$, $\lambda$ $\lambda^2$ and by using the corrected absorbance ($KA_o$) to determine the oil amount, $\alpha_{ow}$, of the wax from said formula for $\alpha_{ow}$ where $$R_{wo} = \frac{A_w \cdot l_o}{A_o \cdot l_w}$$

5. A method as claimed in claim 4, wherein the measurement of $A_w$ and $W_o$ are performed over the wavelength range 316 nm to 500 nm, a first wavelength, $\lambda_1$, is determined as the shortest wavelength in this range for which both $A_w$ and $A_o$ are less than a value representing the upper limit of the linear range of the equipment used for measuring $A_w$ and $A_o$, a second wavelength, $\lambda_2$, is determined as the longest wavelength in this range for which both $A_w$ and $A_o$ are greater than a value representing the noise in said equipment, said correction of the measured absorbance is performed by said least squares regression of the measured was absorbance to $A_o$, $\lambda$ and $\lambda^2$ over the wavelength range from $80_1$ to $80_2$, said value representing the upper limit of the linear range of the equipment used for measuring $A_w$ and $A_o$ is 3.0 AU and said value representing the noise in said equipment is 0.002 AU.

6. A method as claimed in claim 4, wherein the optical pathlengths, $l_w$ and $l_o$, in the oil-bearing wax and the dewaxed oil, respectively, are variable, at least one of these pathlengths being varied until the measured absorbances $A_w$ and $A_o$ are the same and the oil amount, $\alpha_{ow}$, of the wax then being determined from said formula for $\alpha_{ow}$ where $R_{wo}=l_o/l_w$.

7. A method as claimed in claim 4, wherein $l_o$ is selected as equal to a minimum optical pathlength, $l_{min}$, (where $l_{min} \geq 0.5$ mm) and a wavelength $\lambda$ is selected for which the absorbance of the dewaxed oil over the pathlength $l_{min}$ is equal to a specified maximum value $A_{max}$ (where $A_{max} \leq 3$) for the absorbance of the dewaxed oil at a wavelength, $\lambda$, said maximum value not exceeding the upper limit of linearity of the equipment used for measuring $A_o$, and wherein the optical pathlength is varied to determine an optical pathlength $l$ for which the absorbance of the dewaxed oil is equal to $A_{max}$, and the oil amount, $\alpha_{ow}$, of the wax is determined from said formula for $\alpha_{ow}$ where $R_{wo}=l_{min}/l$.

8. A method of separating a fluid mixture 0 into M constituents 1,...,M and of spectroscopically determining the amount $\alpha_{N0}$ of one constituent N of said fluid mixture 0 in that mixture (where $N \leq M$), said method comprising the steps of:
(i) performing the separation of the fluid mixture into its M constituents;
(ii) passing light through constituent N;
(iii) producing a first output representing the absorptivity $a_N$ of constituent N at at least one selected wavelength at which constituent N exhibits light absorption;
(iv) passing light through the fluid mixture 0 prior to the separation;
(v) producing a second output representing the absorptivity $a_0$ of the fluid mixture prior to the separation, at the same at least one selected wavelength; and
(vi) generating, from said first and second outputs, a third output, said third output representing the amount $\alpha_{N0}$ of said one constituent N in the fluid mixture 0, wherein
(vii) the amount of $\alpha_{N0}$ of said one constituent N in the fluid mixture 0 is determined in step (vi) from a mathematical expression in which the functional dependability of $\alpha_{N0}$ on $a_0$ and $a_N$ depends solely on the ratio $a_0/a_N$.

9. A method as claimed in claim 8, wherein the determined amount $\alpha_{N0}$ of said one constituent N in the fluid mixture 0 is used to control one or more parameters of an upstream process producing said fluid mixture 0, so as to minimize differences between the determined amount $\alpha_{N0}$ and a desired value for this amount.

10. Apparatus for separating a fluid mixture 0 into its M constituents (1,...,M) and for the spectroscopic determination of the amount $N_n$ of one constituent N of said fluid mixture 0 in another constituent n (where n, $N \leq M$) of the mixture where, due to imperfect separation, said amount $\alpha_{Nn}$ of constituent N remains present with separated constituent n, said apparatus comprising:
(i) a separator arranged to perform the separation of the fluid mixture into its M constituents;
(ii) means arranged to pass light through constituent N and to determine the absorptivity $a_N$ of said one constituent N at at least one selected wavelength at which constituent N exhibits light absorption and arranged also to pass light through constituent N and to determine the absorptivity $a_n$ of said another constituent n with said amount $\alpha_{Nn}$ of constituent N present at the same at least one selected wavelength; and
(iii) computer means arranged to (a) compute the amount $\alpha_{Nn}$ of said one constituent N present with constituent n from a mathematical expression in which the functional dependability of $\alpha_{Nn}$ on $a_n$ and $a_N$ depends solely on the ratio $a_n/a_N$ and (b) control the operation of the separator in dependence on the computer amount $\alpha_{Nn}$, so as to minimise variations between the computed $\alpha_{Nn}$ and a desired value for $\alpha_{Nn}$.

11. Apparatus as claimed in claim 10, wherein the absorptivity determining means is provided with sampling means operable under the control of the computer means to repeatedly and sequentially feed portions of constituents n and N from the separator through the absorptivity determining means, for enabling the absorptivities $a_n$ and $a_N$ of constituents n and N to be determined.

12. Apparatus as claimed in claim 10, wherein the absorptivity determining means is provided with fiber optic probes each arranged to detect the intensity of light which has passed through a respective one, n, of the M constituents resulting from the separation and to guide the detected light to the absorptivity determining means which is arranged to measure the absorptivity of the light received from the fiber optic probes sequentially under the control of the computer means.

13. Apparatus separating a fluid mixture 0 into is M constituents (1,...,M) and for the spectroscopic determination of the amount $\alpha_{N0}$ of one constituent N of said fluid mixture 0 in the fluid mixture itself following the separation of said mixture into said constituents 1,...,M (where $N \leq M$), said apparatus comprising:
(i) a separator arranged to perform the separation of the fluid mixture into its M constituents;
(ii) means arranged to pass light through constituent N and to determine the absorptivity $a_N$ of said one constituent N at at least one selected wavelength at which constituent N exhibits light absorptivity and arranged also to pass light through constituent N and to determine the absorptivity $a_0$ of said fluid mixture 0 at the same at least one selected wavelength; and
(iii) computer means arranged to (a) compute the amount $\alpha_{N0}$ of said one constituent N from a mathematical expression in which the functional dependability of $\alpha_{N0}$ on $a_n$ and $a_N$ depends solely on the ratio $a_0/a_N$ and (b) control the operation of the separator in dependence on the computer amount $\alpha_{N0}$, so as to minimise variations between the computed amount $\alpha_{N0}$ and a desired value for $\alpha_{Nn}$.

* * * * *